United States Patent
Waszak et al.

(10) Patent No.: US 10,094,765 B2
(45) Date of Patent: Oct. 9, 2018

(54) SENSOR FOR SPECTROMETRIC ANALYSIS OF A VARIABLE-PRESSURE GASEOUS FUEL FOR AUTOMOTIVE VEHICLE

(71) Applicants: CONTINENTAL AUTOMOTIVE FRANCE, Toulouse (FR); CONTINENTAL AUTOMOTIVE GMBH, Hannover (DE)

(72) Inventors: Wladia Waszak, Saint Just (FR); Xavier Bajul, Calmont (FR)

(73) Assignees: CONTINENTAL AUTOMOTIVE FRANCE, Toulouse (FR); CONTINENTAL AUTOMOTIVE GMBH, Hannover (DE)

( * ) Notice: Subject to any disclaimer, the term of this patent is extended or adjusted under 35 U.S.C. 154(b) by 0 days.

(21) Appl. No.: 15/556,594

(22) PCT Filed: Mar. 9, 2016

(86) PCT No.: PCT/EP2016/000418
§ 371 (c)(1),
(2) Date: Sep. 7, 2017

(87) PCT Pub. No.: WO2016/142062
PCT Pub. Date: Sep. 15, 2016

(65) Prior Publication Data
US 2018/0052097 A1    Feb. 22, 2018

(30) Foreign Application Priority Data
Mar. 12, 2015 (FR) .................................. 15 52052

(51) Int. Cl.
*G01N 21/00* (2006.01)
*G01N 21/03* (2006.01)
(Continued)

(52) U.S. Cl.
CPC ....... *G01N 21/0303* (2013.01); *F02D 19/022* (2013.01); *F02D 41/0027* (2013.01);
(Continued)

(58) Field of Classification Search
CPC .. G01N 21/39; G01N 21/3504; G01N 21/031; G01N 2021/399; G01J 3/42
(Continued)

(56) References Cited

U.S. PATENT DOCUMENTS 4,007,722 A * 2/1977 Knapp .................. F02M 69/22
                                                            123/453
5,168,367 A   12/1992 O'Rourke et al.
(Continued)

FOREIGN PATENT DOCUMENTS

DE    33 39 950 A1    5/1985
JP    S61-194334 A    8/1986
(Continued)

OTHER PUBLICATIONS

International Search Report, dated Jun. 17, 2016, from corresponding PCT application No. PCT/EP2016/000418.

*Primary Examiner* — Md M Rahman
(74) *Attorney, Agent, or Firm* — Young & Thompson

(57) ABSTRACT

Disclosed is a sensor for spectrometric analysis of a variable-pressure gaseous fuel for automotive vehicle intended to be mounted in the flow circuit for the fuel linking the fuel tank to the engine of the vehicle. The sensor includes a circulation pipe for the variable-pressure gaseous fuel, a sliding guidance tube for an optical flux and a unit for displacement of the sliding guidance tube, on the basis of the variable-pressure gaseous fuel tapped off from the circulation pipe, so as to adapt the distance separating the first window from the second window as a function of the
(Continued)

variation in pressure of the variable-pressure gaseous fuel circulating in the circulation pipe.

20 Claims, 2 Drawing Sheets

(51) Int. Cl.
F02D 41/14 (2006.01)
G01N 21/3504 (2014.01)
G01N 21/05 (2006.01)
F02D 41/00 (2006.01)
F02D 19/02 (2006.01)
G01N 21/25 (2006.01)

(52) U.S. Cl.
CPC ......... F02D 41/1451 (2013.01); G01N 21/05 (2013.01); G01N 21/255 (2013.01); G01N 21/3504 (2013.01); F02D 2200/0611 (2013.01); G01N 2021/036 (2013.01); G01N 2201/08 (2013.01)

(58) Field of Classification Search
USPC ........................................................ 356/437
See application file for complete search history.

(56) References Cited

U.S. PATENT DOCUMENTS

| 5,268,736 A | 12/1993 | Prather | |
| 2011/0042476 A1* | 2/2011 | McAlister | F02M 57/005 239/5 |
| 2014/0238032 A1* | 8/2014 | Fitzgerald | F02C 9/26 60/772 |

FOREIGN PATENT DOCUMENTS

| JP | H11-229949 A | 8/1999 |
| JP | 2005-221298 A | 8/2005 |
| NL | 1003961 C2 | 3/1998 |

* cited by examiner

SENSOR FOR SPECTROMETRIC ANALYSIS OF A VARIABLE-PRESSURE GASEOUS FUEL FOR AUTOMOTIVE VEHICLE

The invention relates to the field of electronic sensors used in automotive vehicles, and more particularly to a sensor for spectrometric analysis of a variable-pressure gaseous fuel for automotive vehicles, and also to an automotive vehicle comprising such a sensor.

BACKGROUND OF THE INVENTION

In an automotive vehicle, there is a known method of using a sensor for spectrometric analysis of the vehicle's fuel. Thus, sensors for spectrometric analysis of liquid fuel such as gasoline or diesel fuel, for example, and sensors for spectrometric analysis of pressurized variable-pressure gaseous fuel such as methane or dihydrogen for example, are known.

Such sensors are fitted in the fuel routing circuit linking the fuel tank to the engine, and comprise, in a known way, a tube through which the fuel flows. This tube comprises two transparent or translucent portions, called windows, positioned facing one another so as to allow the passage of an optical flow through the fuel flowing in the tube.

Having passed through the tube, and consequently through the fuel flowing in the tube, the optical flow is received by a receiver, which performs a spectrometric analysis on it in a known way to determine the composition of the fuel. This analysis of the fuel composition may be used by an electronic control unit of the vehicle, for example in order to optimize the injection of the fuel into the engine.

In a sensor for spectrometric analysis of a variable-pressure gaseous fuel, the distance between the two windows for the passage of the optical flow, called the optical path, depends on the pressure of the gas to be measured. Thus, for example, the value of the optical path must be large for low-pressure gases, for example 10 mm, whereas the value of the optical path for high-pressure gases must be small, for example 2 mm.

Thus, if the optical path is not adapted to the gas pressure, the signal generated by the sensor may be noisy, that is to say imprecise. This may result in an incorrect spectrometric analysis, which is a major problem. Consequently, if the gas pressure varies over time, the optical path is not necessarily adapted to the different pressure values of the gas flowing in the sensor.

SUMMARY OF THE INVENTION

The aim of the present invention is to overcome this disadvantage by proposing a solution for the spectrometric analysis of gas at different pressures, including both low and high pressures, which is simple, reliable and effective.

For this purpose, the invention relates to a sensor for spectrometric analysis of a variable-pressure gaseous fuel for automotive vehicles, said sensor comprising:
 a body comprising a conduit for the flow of the variable-pressure gaseous fuel,
 an optical flow transmitter,
 a sliding guide tube for said optical flow, comprising a proximal end coupled to the transmitter and a distal end comprising a first window opening into the flow conduit and configured to allow the passage of the optical flow,
 a second window positioned facing the first window so as to allow the optical flow to pass through the flow conduit,
 a receiver of said optical flow, configured to receive and analyze the optical flow received through the second window,
 a channel for sampling variable-pressure gaseous fuel from the flow conduit, and
 means for moving the sliding guide tube on the basis of variable-pressure gaseous fuel sampled from the flow conduit via the sampling channel, for the purpose of adapting the distance between the first window and the second window on the basis of the pressure variation of the variable-pressure gaseous fuel flowing in the flow conduit.

The term "optical flow" is taken to mean a flow of light waves used for the spectrometric analysis of a variable-pressure gaseous fuel.

The sensor according to the invention is intended to be fitted in the fuel routing circuit linking a fuel tank to the engine of the vehicle, or directly in a fuel tank of the vehicle.

The sensor according to the invention therefore advantageously enables the optical path to be adapted on the basis of pressure variations of the variable-pressure gaseous fuel. Thus the sensor generates a low signal to noise ratio, regardless of the pressure value of the variable-pressure gaseous fuel, thereby significantly improving the precision of the spectrometric analysis.

Advantageously, the distal end of the sliding guide tube comprises a first ring, and the first window is fitted in the center of said first ring.

According to an aspect of the invention, the first window and the second window are transparent and/or translucent, so as to allow the passage of the optical flow.

Preferably, the first window and the second window each take the form of a bowl, made of glass or plastic material for example, which is easily produced.

Also preferably, the means for moving the sliding guide tube comprise a compression spring fitted around the sliding guide tube and an element for driving said spring.

According to an aspect of the invention, the drive element comprises a second ring fixed to the sliding guide tube and extending radially from the outer wall of the sliding guide tube.

This second ring delimits, on one side, a receiving space for variable-pressure gaseous fuel, and, on the opposite side, an expansion space in which the compression spring extends.

The second ring is configured to receive a pressure exerted by the variable-pressure gaseous fuel.

Advantageously, the sliding guide tube comprises a wall of cylindrical shape for retaining the compression spring, extending from the second ring into the expansion space.

According to a characteristic of the invention, the channel for sampling variable-pressure gaseous fuel opens into the receiving space.

Advantageously, the body of the sensor comprises an air flow channel linking the expansion space to the space outside the sensor.

Also preferably, the sliding guide tube extends along a longitudinal axis orthogonal to the longitudinal axis of the flow conduit.

According to another characteristic of the invention, the sensor comprises a plurality of seals, such as ring seals, positioned between the body and the sliding guide tube, for the purpose, notably, of providing a seal, on the one hand, between the receiving space and the space outside the sensor, and, on the other hand, between the expansion space and the flow conduit.

The invention also relates to a vehicle comprising at least one variable-pressure gaseous fuel tank, at least one engine supplied with variable-pressure gaseous fuel, a circuit for routing variable-pressure gaseous fuel from said tank to said engine, and a spectrometric analysis sensor as described above, positioned in said routing circuit or in the tank in order to determine the composition of the variable-pressure gaseous fuel flowing in the routing circuit or stored in the reservoir.

BRIEF DESCRIPTION OF THE DRAWINGS

Other characteristics and advantages of the invention will be apparent from the following description which refers to the attached drawings, provided by way of non-limiting examples, in which identical references are given to similar objects.

DETAILED DESCRIPTION OF THE PREFERRED EMBODMENTS

The sensor described below with reference to FIGS. 1 to 4 is intended to be fitted in a circuit (not shown) for supplying variable-pressure gaseous fuel between a variable-pressure gaseous fuel tank and an engine of an automotive vehicle. However, it should be noted that, in a variant, the sensor according to the invention could be fitted directly in a fuel tank of the vehicle.

The object of the sensor according to the invention is to carry out spectrometric analysis of variable-pressure gaseous fuel.

Figure 2:
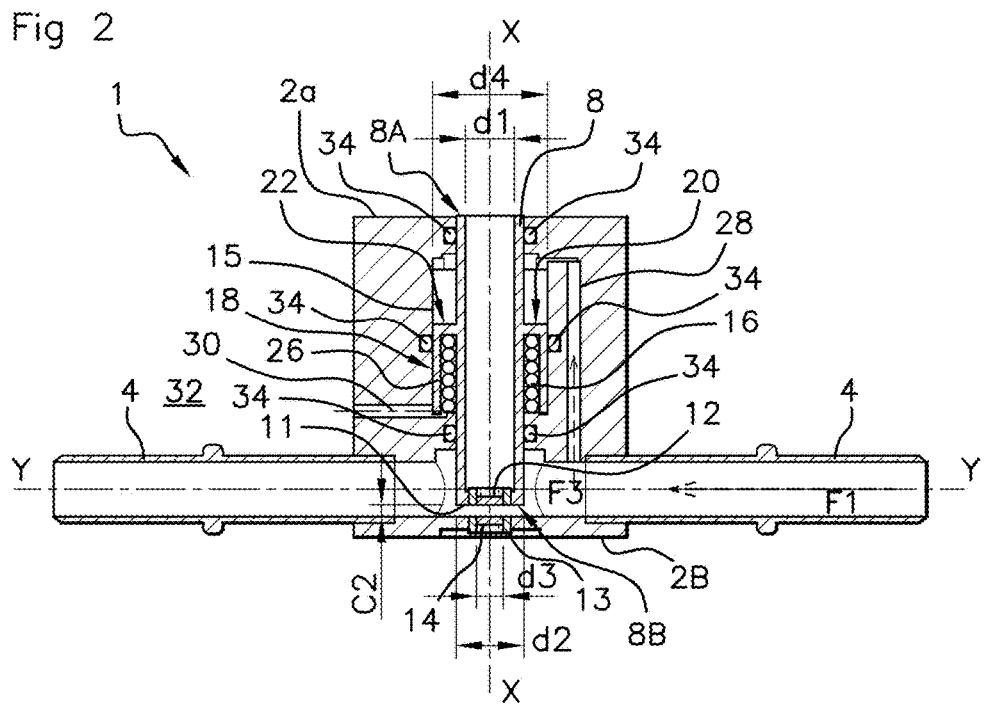
FIG. 2 is a view in longitudinal section of an embodiment of the sensor according to the invention in a position of use.
Figure 3:
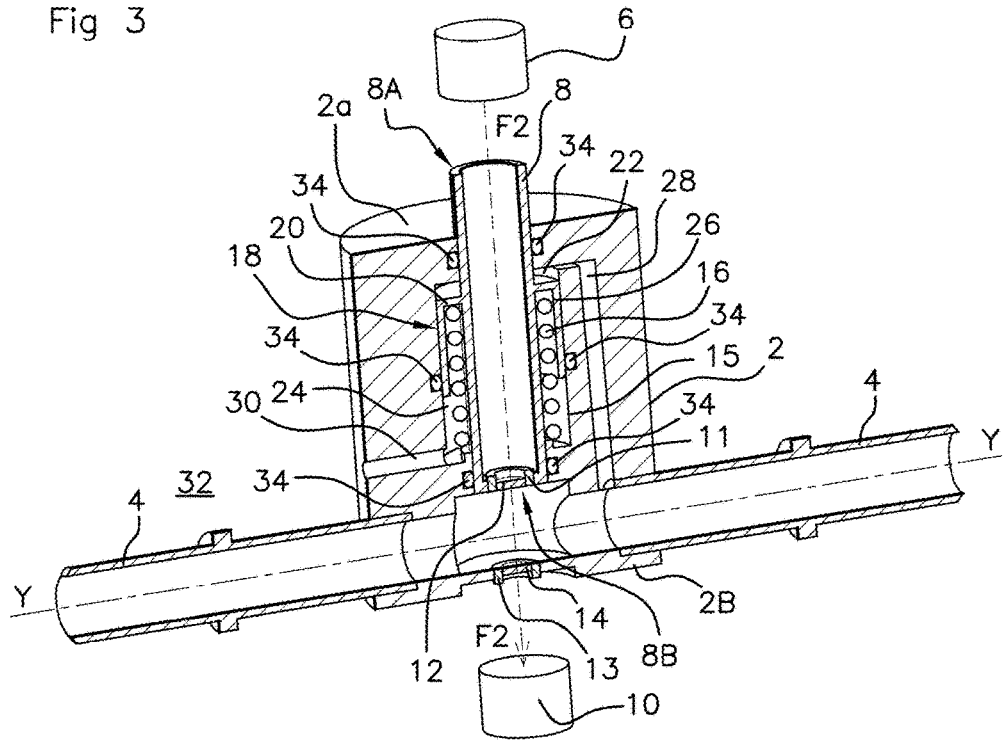
FIG. 3 is a perspective view of the embodiment shown in FIG. 1.
Figure 4:
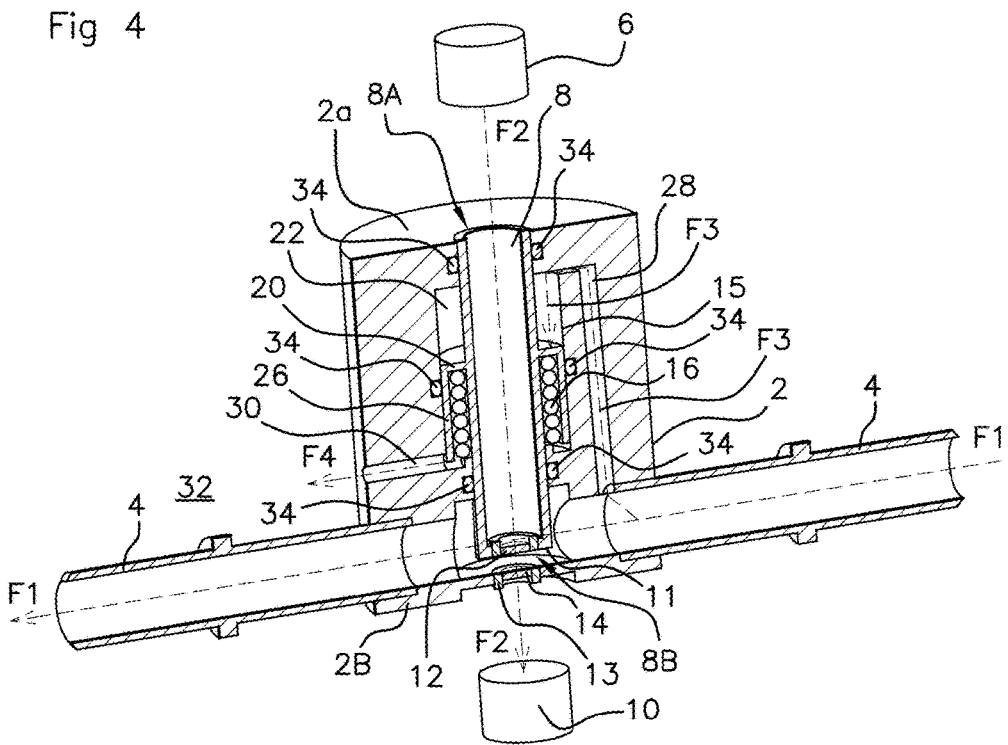
FIG. 4 is a perspective view of the embodiment shown in FIG. 2.

With reference to FIGS. 1 to 4, the sensor 1 comprises, firstly, a cylindrical body 2 and a conduit 4 for the passage of a flow F1 of variable-pressure gaseous fuel (with reference to FIG. 4).

The cylindrical body 2 extends along a longitudinal axis X-X and comprises a first end 2A and a second end 2B.

The conduit 4 for the passage of a flow F1 of variable-pressure gaseous fuel extends from said body 2 along a longitudinal axis Y-Y orthogonal to the longitudinal axis X-X of the body 2. It should be noted that this flow conduit 4 may be fitted on the body 2 or may be made directly in one piece with the body 2. In this preferred example, the flow conduit 4 is fitted at the second end 2B of the body 2, although this does not limit the scope of the present invention.

The sensor 1 further comprises a transmitter 6 of an optical flow F2 (i.e. a flow of light), with reference to FIGS. 3 and 4, a sliding guide tube 8 for said optical flow F2 and a receiver 10 for said optical flow F2. The optical flow F2 is transmitted by the transmitter 6 through the sliding guide tube 8. Such a transmitter 6 is known to those skilled in the art and will not be detailed further.

In this example, again with reference to FIGS. 1 to 4, the longitudinal axis Y-Y of the body 2 and the longitudinal axis of the sliding guide tube 8 coincide. In other words, the sliding guide tube 8 and the body 2 are coaxial about the longitudinal axis Y-Y.

With reference to FIG. 2, the sliding guide tube 8 defines an inside diameter d1 and an outside diameter d2.

Figure 1:
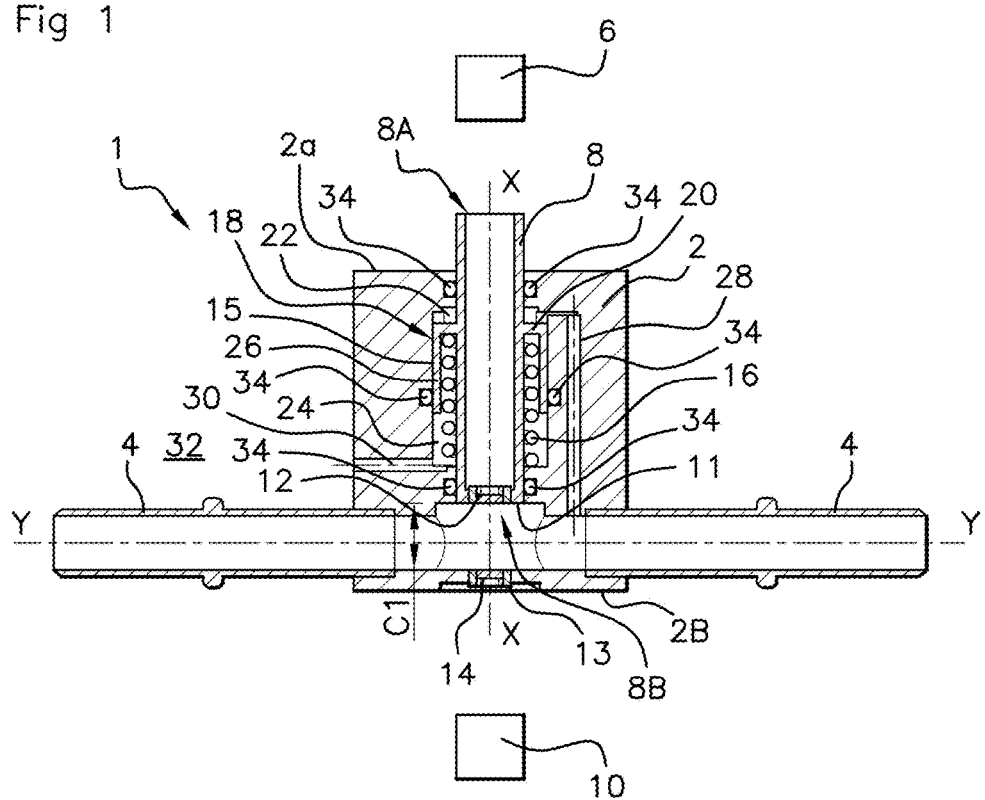
FIG. 1 is a view in longitudinal section of an embodiment of the sensor according to the invention in the rest position.

The sliding guide tube 8 comprises a proximal end 8A, which is coupled to said transmitter 6 and can extend outside the body 2 as shown in FIGS. 1 and 3, and a distal end 8B which can extend into the flow conduit 4 and comprises a first ring 11 in the center of which a first window 12 is fitted.

For the sake of clarity, the coupling of the transmitter 6 to the sliding guide tube 8, which is known to those skilled in the art, has not been shown in the drawings. By way of example, it will be pointed out that the transmitter 6 may be connected to the proximal end 8A of the sliding guide tube 8, via an optical fiber for example, or may be fitted on or in the proximal end 8A of the sliding guide tube 8.

The first window 12 takes the form of a cylindrical bowl with a small thickness, of 1 or 2 mm for example, with a diameter d3, of about 6 mm for example, made of a transparent or translucent material, for example a plastic or glass material, and having an axis of revolution coinciding with the longitudinal axis Y-Y.

This first window 12 is configured to allow the passage of the optical flow F2, while preventing the entry of the variable-pressure gaseous fuel into the sliding guide tube 8.

The sensor 1 comprises, at the second end 2B of the body 2 on which the flow conduit 4 is fitted, a circular support frame 13, in the center of which is fitted a second window 14 positioned facing the first window 12, with respect to the longitudinal axis Y-Y of the flow conduit 4, in such a way that the optical flow F2 transmitted by the transmitter 6 in the sliding guide tube 8 passes successively through the first window 12, then the flow conduit 4, and then the second window 14, before reaching the receiver 10.

In a similar way to the first window 12, this second window 14 takes the form of a cylindrical bowl with a small thickness, of 1 or 2 mm for example, with a diameter d3, of about 6 mm for example, made of a transparent or translucent material, for example a plastic or glass material, and having an axis of revolution coinciding with the longitudinal axis Y-Y.

This second window 14 is configured to allow the passage of the optical flow while preventing the exit of the variable-pressure gaseous fuel from the flow conduit 4.

The receiver 10 is configured to receive the optical flow F2 which is transmitted by the transmitter 6 in the sliding guide tube 8 and which has passed successively through the first window 12, the flow conduit 4 and the second window 14.

In this example, the receiver 10 is also configured to perform a spectrometric analysis of the received optical flow F2 in order to determine the composition of the flow F1 of variable-pressure gaseous fuel flowing in the flow conduit 4.

In another embodiment, it should be noted that the spectrometric analysis could be performed by an entity placed outside the receiver 10 but connected to the latter. Such a spectrometric analysis is known to those skilled in the art and will therefore not be detailed further.

According to the invention, the sliding guide tube 8 is fitted slidably in the body 2 in a guide conduit 15 formed in said body 2.

More precisely, the sliding guide tube 8 is configured to slide between a rest position shown in FIGS. 1 and 3, characterized by the absence of a flow of fuel in the flow conduit 4, and a plurality of positions of use of the sensor, of which one example of a position is shown in FIGS. 2 and 4, characterized by the passage of a pressurized variable-pressure gaseous fuel.

For this purpose, the sensor 1 comprises means for moving the sliding guide tube 8. These movement means comprise a compression spring 16 fitted around the sliding guide tube 8 and a drive element 18 for driving said spring 16.

In the embodiment shown in FIGS. 1 to 4, this drive element 18 comprises a second ring 20 fixed to the sliding guide tube 8, extending radially from the outer wall of the sliding guide tube 8, and having an axis of revolution coaxial with the longitudinal axis Y-Y of the sliding guide tube 8.

This second ring 20, with an outside diameter d4, delimits, on one side, a receiving space 22 for variable-pressure gaseous fuel, and, on the opposite side, an expansion space 24 in which the compression spring 16 extends.

In order, notably, to retain and compress the compression spring 16, the sliding guide tube 8 comprises a retaining wall 26 of cylindrical shape, having an outside diameter slightly smaller than d4 so that it can be moved in the expansion space 24, extending from the second ring 20 against the walls of the expansion space 24 toward the flow conduit 4, parallel to the longitudinal axis Y-Y of the sliding guide tube 8.

The second ring 20 is configured to receive a pressure exerted by the variable-pressure gaseous fuel, in order to drive the sliding guide tube 8 in translation.

For this purpose, the sensor 1 according to the invention comprises a channel 28 for sampling variable-pressure gaseous fuel from the flow conduit 4, opening into the receiving space 22, and an air passage channel 30 linking the expansion space 24 to the space 32 outside the sensor 1.

Finally, the sensor 1 comprises a plurality of seals 34, such as ring seals, positioned between the body 2 and the sliding guide tube 8, for the purpose, notably, of providing a seal, on the one hand, between the receiving space 22 and the space 32 outside the sensor 1, and, on the other hand, between the expansion space 24 and the flow conduit 4.

The invention will now be described in its application.

When the sensor is in operation, with reference to FIGS. 3 and 4, the transmitter 6 transmits an optical flow F2 into the sliding guide tube 8 so that this optical flow F2 passes through said sliding guide tube 8 from its proximal end 8A to its distal end 8B where it passes through the first window 12, then transversely through the flow conduit 4, and then through the second window 14, until it reaches the receiver 10.

In the absence of variable-pressure gaseous fuel in the flow conduit 4, that is to say in the absence of a flow F1 of gas in the flow conduit 4, no variable-pressure gaseous fuel flows in the sampling channel 28, and therefore no pressure is exerted on the second ring 20.

In this case, as shown in FIGS. 1 and 3, the sliding guide tube 8 is in its rest position, the proximal end 8A of the sliding guide tube 8 extending outside 32 the body 2 at its first end 2B, the spring 18 is not compressed, and the distance C1 between the first window 12 and the second window 14 is maximal.

When pressurized variable-pressure gaseous fuel flows in the flow conduit 4, a fraction of this variable-pressure gaseous fuel is sampled in the form of a flow F3 by the sampling channel 28 and is then routed to the receiving space 22.

With reference to FIGS. 2 and 4, under the pressure of this fraction of variable-pressure gaseous fuel on the second ring 20 bearing on the compression spring 16, the spring 16 is compressed so as to cause the sliding guide tube 8 to slide in the guide conduit 15 toward the inside of the flow conduit 4 and thus reduce the distance between the first window 12 and the second window 14.

In the example shown in FIGS. 2 and 4, the pressure of the variable-pressure gaseous fuel is such that the spring 16 is compressed to the maximum extent, corresponding to a minimum distance C2 between the first window 12 and the second window 14.

This sliding of the sliding guide tube 8 in the guide conduit 15 is, notably, made possible by the discharge of the air located in the expansion space 24 toward the outside 32 of the sensor 1 through the flow channel 30, in the form of a flow F4.

Thus, with the sensor according to the invention, as the pressure of the variable-pressure gaseous fuel increases, the distance between the first window 12 and the second window 14 decreases, within the limits of compression of the spring 16.

The contact surface of the second ring 20 in the receiving space 22 and the compression rate of the spring 16 must therefore be selected in such a way as to adapt the distance between the first window 12 and the second window 14 to the value required for the performance of a reliable spectrometric analysis.

Thus, by way of example, the means for moving the sliding guide tube 8 may be designed as follows.

The zero pressure, or a minimum threshold value of the pressure $P_{min}$, of the variable-pressure gaseous fuel may correspond to the maximum distance C1 between the first window 12 and the second window 14 (the maximum optical path).

The maximum pressure $P_{max}$ (or a maximum threshold value of the pressure) of the variable-pressure gaseous fuel may correspond to the minimum distance C2 between the first window 12 and the second window 14 (the minimum optical path). The mechanical equilibrium of the means for moving the sliding guide tube 8 is governed by the following equation:

$$P \times S_2 = (P \times S_1) + F_r$$

where:

P is the pressure of the variable-pressure gaseous fuel flowing from the flow conduit 4 and into the sampling channel 28, $S_1$ is the contact surface between the first ring 11 of the sliding guide tube 8, whose diameter is equal to the outside diameter d2 of the sliding guide tube 8, and the gas contained in the flow conduit 4, $S_2$ is the contact surface between the second ring 20 and the gas contained in the receiving space 22, and $F_r$ is the force exerted by the compression spring 16.

The pre-stress or pre-loading $F_{r1}$ of the spring 16 (the force of the spring 16 in the rest position of the sliding guide tube 8) must be greater than or equal to the axial component of the frictional resistance of the set of dynamic seals.

Let us consider the minimum pressure $P_{min}$ of the gaseous fuel, when the force $F_r$ exerted by the compression spring 16 is equal to the pre-stress $F_{r1}$ of the spring 16, the spring 16 is in its pre-stressed, uncompressed state, and the guide tube 8 is in the position where the distance between the first window 12 and the second window 14 is maximal, being equal to C1.

Using the equilibrium equation, at $P=P_{min}$, we find:

$$P_{min} \times S_2 = (P_{min} \times S_1) + F_{r1}$$

Therefore:

$$S_2 = \frac{\left(P_{min} \times \pi \times \frac{d_2^2}{4}\right) + F_{r1}}{P_{min}}$$

where
$d_2$ is the outside diameter of the sliding guide tube, and $\pi$ is a constant equal to 3.14.

Let us consider the maximum pressure $P_{max}$ of the gaseous fuel, when the force $F_r$ exerted by the compression spring 16 is equal to the maximum force $F_{r2}$ of the spring 16, the spring 16 is compressed, and the guide tube 8 is in the position where the distance between the first window 12 and the second window 14 is minimal, being equal to C2.

Using the equilibrium equation, we find:

$$P \times S_2 = (P_{max} \times S_1) + F_{r2}$$

$$F_{r2} = P_{max} \times \left(S_2 - \pi \times \frac{d_2^2}{4}\right)$$

where $P_{max}$ is the maximum (threshold) pressure value of the variable-pressure gaseous fuel.

where
$d_2$ is the outside diameter of the sliding guide tube, and $\pi$ is a constant equal to 3.14.

The stiffness $R_r$ of the spring 16 is then defined by the following equation:

$$R_r = \frac{F_{r2} - F_{r1}}{C1 - C2}$$

where:
C1 is the maximum distance between the first window 12 and the second window 14, and
C2 is the minimum distance between the first window 12 and the second window 14.

When the pressure of the variable-pressure gaseous fuel decreases, the pressure exerted on the second ring 20 also decreases, so that the compression of the spring 16 is reduced, thereby again increasing the distance between the first window 12 and the second window 14. This is again made possible by the presence of the flow channel 30 which, in this case, allows external air to be drawn into the expansion space 24.

When the flow of the variable-pressure gaseous fuel in the flow conduit ceases, or when the fuel is not under pressure (that is to say, when its pressure is equal to atmospheric pressure), the spring 16 returns to its position of maximum expansion, and the sliding guide tube is then once again in its rest position as shown in FIGS. 1 and 3.

The method according to the invention thus advantageously enables the distance between the first window 12 and the second window 14 to be adapted; that is to say it enables the length of the optical path to be adapted on the basis of the pressure of the variable-pressure gaseous fuel, thereby allowing a reliable spectrometric analysis to be performed on the variable-pressure gaseous fuel flowing in the flow conduit 4.

Finally, it should be noted that the present invention is not limited to the examples described above and can be varied in numerous ways within the capacity of those skilled in the art. Notably, the shape and dimensions of the body 2, of the flow conduit 4, of the sliding guide tube 8, and of the means for moving the sliding guide tube 8, as shown in the figures to illustrate an example of embodiment of the invention, are not to be interpreted as limiting.

The invention claimed is:

1. A sensor for spectrometric analysis of a variable-pressure gaseous fuel for an automotive vehicle, said sensor, comprising:
    a body comprising a conduit for the flow of the variable-pressure gaseous fuel;
    a transmitter of an optical flow;
    a sliding guide tube for said optical flow, comprising a proximal end coupled to the transmitter and a distal end comprising a first window opening into the flow conduit and configured to allow the passage of the optical flow;
    a second window positioned facing the first window so as to allow the optical flow to pass through the flow conduit;
    a receiver of said optical flow, configured to receive and analyze the optical flow received through the second window; and
    a channel for sampling variable-pressure gaseous fuel from the flow conduit,
    wherein the sliding guide tube is movable responsive to variable-pressure gaseous fuel sampled from the flow conduit via the sampling channel such that a distance between the first window and the second window changes on the basis of a pressure variation of the variable-pressure gaseous fuel flowing in the flow conduit,
    said sliding guide tube comprising a driving element comprising a second ring fixed to the sliding guide tube and extending radially from the outer wall of the sliding guide tube, and a compression spring fitted around the sliding guide tube configured to urge against the driving element, and
    wherein the second ring delimits, on a first side, a receiving space for variable-pressure gaseous fuel, and on an opposite second side, an expansion space in which the compression spring is located.

2. The sensor as claimed in claim 1, wherein the distal end of the sliding guide tube comprises a first ring, the first window being fitted in the center of said first ring.

3. The sensor as claimed in claim 2, wherein the body of the sensor comprises an air flow channel linking the expansion space to the space outside the sensor.

4. The sensor as claimed in claim 2, said sensor comprising a plurality of seals positioned between the body and the sliding guide tube.

5. A vehicle comprising at least one variable-pressure gaseous fuel tank, at least one engine supplied with variable-pressure gaseous fuel, a circuit for routing variable-pressure gaseous fuel from said tank to said engine, and the sensor for spectrometric analysis as claimed in claim 2, positioned in said routing circuit or in the tank in order to determine the composition of the variable-pressure gaseous fuel flowing in the routing circuit or stored in said reservoir.

6. The sensor as claimed in claim 1, wherein the sliding guide tube comprises a wall of cylindrical shape for retaining the compression spring, extending from the second ring into the expansion space.

7. The sensor as claimed in claim 6, wherein the channel for sampling variable-pressure gaseous fuel opens into the receiving space.

8. The sensor as claimed in claim 6, wherein the body of the sensor comprises an air flow channel linking the expansion space to the space outside the sensor.

9. The sensor as claimed in claim 6, said sensor comprising a plurality of seals positioned between the body and the sliding guide tube.

10. A vehicle comprising at least one variable-pressure gaseous fuel tank, at least one engine supplied with variable-pressure gaseous fuel, a circuit for routing variable-pressure gaseous fuel from said tank to said engine, and the sensor for spectrometric analysis as claimed in claim 6, positioned in said routing circuit or in the tank in order to determine the composition of the variable-pressure gaseous fuel flowing in the routing circuit or stored in said reservoir.

11. The sensor as claimed in claim 1, wherein the channel for sampling variable-pressure gaseous fuel opens into the receiving space.

12. The sensor as claimed in claim 11, wherein the body of the sensor comprises an air flow channel linking the expansion space to the space outside the sensor.

13. The sensor as claimed in claim 11, said sensor comprising a plurality of seals positioned between the body and the sliding guide tube.

14. A vehicle comprising at least one variable-pressure gaseous fuel tank, at least one engine supplied with variable-pressure gaseous fuel, a circuit for routing variable-pressure gaseous fuel from said tank to said engine, and the sensor for spectrometric analysis as claimed in claim 11, positioned in said routing circuit or in the tank in order to determine the composition of the variable-pressure gaseous fuel flowing in the routing circuit or stored in said reservoir.

15. The sensor as claimed in claim 1, wherein the body of the sensor comprises an air flow channel linking the expansion space to the space outside the sensor.

16. The sensor as claimed in claim 15, said sensor comprising a plurality of seals positioned between the body and the sliding guide tube.

17. A vehicle comprising at least one variable-pressure gaseous fuel tank, at least one engine supplied with variable-pressure gaseous fuel, a circuit for routing variable-pressure gaseous fuel from said tank to said engine, and the sensor for spectrometric analysis as claimed in claim 15, positioned in said routing circuit or in the tank in order to determine the composition of the variable-pressure gaseous fuel flowing in the routing circuit or stored in said reservoir.

18. The sensor as claimed in claim 1, said sensor comprising a plurality of seals positioned between the body and the sliding guide tube.

19. A vehicle comprising at least one variable-pressure gaseous fuel tank, at least one engine supplied with variable-pressure gaseous fuel, a circuit for routing variable-pressure gaseous fuel from said tank to said engine, and the sensor for spectrometric analysis as claimed in claim 18, positioned in said routing circuit or in the tank in order to determine the composition of the variable-pressure gaseous fuel flowing in the routing circuit or stored in said reservoir.

20. A vehicle comprising at least one variable-pressure gaseous fuel tank, at least one engine supplied with variable-pressure gaseous fuel, a circuit for routing variable-pressure gaseous fuel from said tank to said engine, and the sensor for spectrometric analysis as claimed in claim 1, positioned in said routing circuit or in the tank in order to determine the composition of the variable-pressure gaseous fuel flowing in the routing circuit or stored in said reservoir.

* * * * *